US00H002290H

(19) United States
(12) Statutory Invention Registration
Vargas et al.

(10) Reg. No.: US H2290 H
(43) Published: Apr. 1, 2014

(54) HIGH STRENGTH PRESULFIDED CATALYST FOR HYDROGENATING HYDROCARBON RESINS

(75) Inventors: Jose M. Vargas, Friends Wood, TX (US); Thomas R. Barbee, Kingwood, TX (US); Yuan-Ju Chen, Houston, TX (US)

(73) Assignee: ExxonMobil Chemical Patents Inc., Houston, TX (US)

(21) Appl. No.: 13/352,012

(22) Filed: Jan. 17, 2012

(65) Prior Publication Data

US 2013/0184411 A1 Jul. 18, 2013

(51) Int. Cl.
*B01J 31/26* (2006.01)
*C07C 5/02* (2006.01)
*C08F 8/04* (2006.01)

(52) U.S. Cl.
USPC ..... 525/343; 502/159; 585/275

(58) Field of Classification Search
USPC ..... 525/343; 502/159; 585/275
See application file for complete search history.

(56) References Cited

U.S. PATENT DOCUMENTS

2013/0184411 A1* 7/2013 Vargas et al. ..... 525/343

* cited by examiner

*Primary Examiner* — Daniel Pihulic

(57) ABSTRACT

High strength presulfided catalyst for hydrogenating hydrocarbon resins without an in situ sulfiding step. The catalyst particles have a supported metal catalyst structure with presulfided interstitial surfaces with about 20 weight percent of a low molecular weight hydrocarbon resin, based on the weight of the porous supported metal catalyst structure, filling from 90 to 95 percent of the pore volume to improve a crush strength of the catalyst particles. The presulfided catalyst can be stored and/or shipped in an airtight container with an inert atmosphere. The catalyst particles are made by preparing the oxidized catalyst, presulfiding the catalyst, contacting the catalyst with the low molecular weight hydrocarbon resin in an inert atmosphere, sealing the catalyst in a storage/shipping container, loading the reactor with the presulfided, filled catalyst, and contacting the catalyst with an unsaturated hydrocarbon resin under hydrogenation conditions.

2 Claims, 1 Drawing Sheet

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

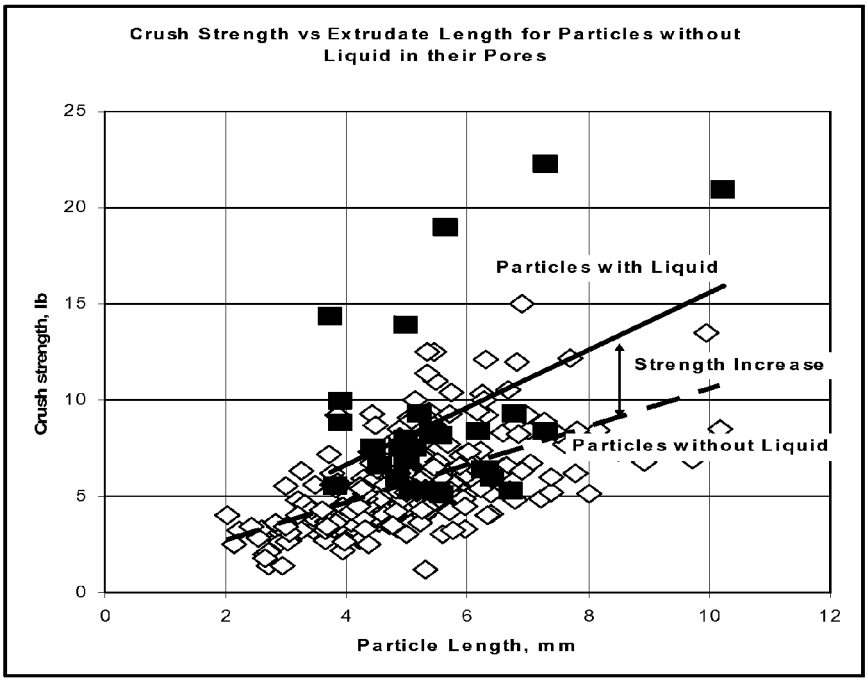
Crush Strength vs Extrudate Length for Particles without Liquid in their Pores
Crush strength, lb
Particle Length, mm
Particles with Liquid
Strength Increase
Particles without Liquid
0
5
10
15
20
25
0
2
4
6
8
10
12

HIGH STRENGTH PRESULFIDED CATALYST FOR HYDROGENATING HYDROCARBON RESINS

CROSS REFERENCE TO RELATED APPLICATIONS

None.

STATEMENT REGARDING FEDERALLY SPONSORED RESEARCH OR DEVELOPMENT

Not applicable.

THE NAMES OF PARTIES TO A JOINT RESEARCH AGREEMENT

Not applicable.

INCORPORATION-BY-REFERENCE OF MATERIAL SUBMITTED ON A CD

Not applicable.

BACKGROUND

The present invention relates to the hydrogenation of hydrocarbon resins and also to the catalysts used for hydrogenating hydrocarbon resins.

Some catalysts used for hydrogenating hydrocarbon resins are sulfided to their active sulfide forms prior to use. In situ sulfidation in the hydrogenation reactor may take as much as 48 hours or more, during which time the hydrogenation reactor is taken out of production.

Some catalysts used for hydrogenating hydrocarbon resins have low crush strength and can easily fracture to produce fines. Low crush strength catalysts generate dust during reactor loading and introduce foulant materials into the reactor. The fines can restrict or block flow passages and undesirably increase the pressure drop through a fixed bed of the hydrogenation catalyst and/or the associated lines and equipment.

There are needs in the art to reduce or eliminate the in situ sulfiding time, and to improve the crush strength of catalyst and reduce the quantity of fines generated from the hydrogenation catalyst.

SUMMARY

In one embodiment, a metal catalyst useful for hydrogenating hydrocarbon resin is sulfided ex situ, passivated and optionally stored for later use. The presulfided catalyst may be loaded into the hydrogenation reactor and is immediately ready for use without any further sulfidation operation in situ. By reducing or eliminating the time required for in situ sulfiding operation, the time normally allocated for sulfiding can be used for additional production.

In another embodiment, a metal catalyst useful for hydrogenating hydrocarbon resin comprises a pore volume at least partially filled with an organic compound to increase crush strength.

In another embodiment, a metal catalyst useful for hydrogenating hydrocarbon resin is contacted with an organic liquid to partially fill a pore volume, and the partially filled catalyst is thereafter loaded into a hydrogenation reactor. The catalyst may be presulfided before, during or after contact with the organic liquid and passivated prior to the catalyst loading into the reactor, or alternatively or additionally the catalyst may be sulfided in situ after the catalyst is loaded into the reactor.

In another embodiment, in a method comprising loading a hydrogenation reactor with supported metal catalyst and preparing the catalyst for hydrogenating a hydrocarbon resin, an improvement comprises sulfiding the catalyst ex situ to reduce or eliminate the in situ preparation time.

In another embodiment, in a method comprising loading a hydrogenation reactor with metal catalyst and contacting the catalyst with hydrocarbon resin under hydrogenation conditions, an improvement comprises partially filling a pore volume of the catalyst with an organic liquid and loading the hydrogenation reactor with the partially filled catalyst. The improvement in one embodiment reduces the formation of catalyst fines. In another embodiment, the improvement reduces a pressure drop through a fixed bed of the catalyst in the hydrogenation reactor.

BRIEF DESCRIPTION OF THE DRAWING

FIG. 1 shows the crush strength vs. extrudate length for catalyst particles with and without an organic liquid disposed in the pores.

DETAILED DESCRIPTION

"Metal" in the context of the catalyst does not necessarily mean the metal in its metallic form but present in any metal compound, such as the metal component as initially applied or as present in a bulk or supported catalyst composition, e.g., metal oxides and/or metal sulfides.

The catalyst referred to herein is generally useful in a process for hydrogenating or hydrotreating (used interchangeably herein) a catalytically or thermally prepared hydrocarbon resin in the presence of the catalyst. Any of the known metal catalysts and/or processes for catalytically hydrogenating hydrocarbon resins can be modified in accordance with the present disclosure by substituting the catalyst system and/or processing steps, in particular the processes and metal catalysts of U.S. Pat. No. 6,755,963; U.S. Pat No. 5,171,793; U.S. Pat. No. 4,629,766; U.S. Pat. No. 4,328,090; EP 0 240 253; EP 0 082 726; and WO 95/12623 are suitable, each of which is referred to and incorporated herein by reference in their entireties for all purposes. A nickel molybdotungstate denitrogenation catalyst which may also be employed herein is disclosed in WO 99/03578, which is incorporated herein by reference in its entirety for all purposes. The nickel molybdotungstate catalyst in WO 99/03578 is prepared by decomposing a nickel (ammonium) molybdotungstate precursor and sulfiding the decomposition product, either pre-use or in situ.

EP 0 082 726 describes a process for the hydrogenation of petroleum resins from catalytic or thermal polymerization of olefin- and diolefin-containing streams, using nickel-tungsten catalyst on a gamma-alumina support wherein the hydrogen pressure is 14.7 MPa to 19.6 MPa and the temperature is in the range of 250° C. to 330° C. The polymerization feed streams are said to contain $C_5$ and/or $C_6$ olefin and/or diolefin streams, and, for catalytic polymerization, $C_8/C_9$ aromatic olefins, e.g., styrene, vinyl benzene and optionally indene. Thermal polymerization is usually done at 160° C. to 320° C., at a pressure of 0.98 MPa to 1.17 MPa and for a period typically of 1.5 to 4 hours. After hydrogenation the reactor mixture may be flashed and further separated to recover the hydrogenated resin. Steam distillation may be used to eliminate oligomers, without exceeding 325° C. resin temperature in one embodiment.

Catalysts employed for the hydrogenation of hydrocarbon resins are typically supported monometallic, bimetallic, or multimetallic catalyst systems based on elements from Group 6, 8, 9, 10, or 11 of the Periodic Table of Elements. Bulk multimetallic catalysts in an embodiment are comprised of at least one Group VIII non-noble metal and at least two Group VIB metals and wherein the ratio of Group VIB metal to Group VIII non-noble metal is from about 10:1 to about 1:10, e.g., a nickel molybdotungstate catalyst, as described in U.S. Pat. No. 6,755,963. In one embodiment, the catalyst is supported, e.g., on an inert material such as metal oxide such as alumina (e.g., gamma-alumina), silica or the like, which may function as a binder to hold the metal catalyst compounds at the interstitial surfaces of the pores. In another embodiment, the catalyst is unsupported, i.e. a bulk catalyst prepared without a binder.

The Group VIB metal in one embodiment comprises chromium, molybdenum, tungsten, or mixtures thereof Group VIII non-noble metals in one embodiment are, e.g., iron, cobalt, nickel, or mixtures thereof. In an embodiment, the catalyst comprises a combination of metal components comprising nickel, molybdenum and tungsten or nickel, cobalt, molybdenum and tungsten. In an embodiment, nickel components used to prepare the catalyst may comprise water-insoluble nickel components, such as, nickel carbonate, nickel hydroxide, nickel phosphate, nickel phosphite, nickel formate, nickel sulfide, nickel molybdate, nickel tungstate, nickel oxide, nickel alloys, such as, nickel-molybdenum alloys, Raney nickel, or mixtures thereof. In an embodiment, molybdenum components used to prepare the catalyst may comprise water-insoluble molybdenum components, such as, molybdenum (di- and tri) oxide, molybdenum carbide, molybdenum nitride, aluminum molybdate, molybdic acid (e.g., $H_2MoO_4$), molybdenum sulfide, or mixtures thereof; or water-soluble nickel components, e.g., nickel nitrate, nickel sulfate, nickel acetate, nickel chloride, or mixtures thereof. In an embodiment, tungsten components used to prepare the catalyst may comprise tungsten di- and trioxide, tungsten sulfide ($WS_2$ and $WS_3$), tungsten carbide, tungstic acid (e.g., $H_2WO_4$-$H_2O$, $H_2W_4O_{13}$-$9H_2O$), tungsten nitride, aluminum tungstate (also meta-, or polytungstate) or mixtures thereof. In an embodiment, the catalyst may be made from and/or contain water-soluble molybdenum and tungsten components, such as, alkali metal or ammonium molybdate (also peroxo-, di-, tri-, tetra-, hepta-, octa-, or tetradecamolybdate), Mo-P heteropolyanion compounds, Wo-Si heteropolyanion compounds, W-P heteropolyanion compounds, W-Si heteropolyanion compounds, Ni-Mo-W heteropolyanion compounds, Co-Mo-W heteropolyanion compounds, alkali metal or ammonium tungstates (also meta-, para-, hexa-, or polytungstate), or mixtures thereof. In an embodiment, combinations of metal components comprising the catalyst are nickel carbonate, tungstic acid and molybdenum oxide; or nickel carbonate, ammonium dimolybdate and ammonium metatungstate.

The hydrogenation catalyst is generally comprised of porous metal and/or support components having a typical total pore volume and pore size distribution of conventional hydrotreating catalysts, e.g., a pore volume of 0.05-5 ml/g, or of 0.1-4 ml/g, or of 0.1-3 ml/g or of 0.1-2 ml/g determined by nitrogen adsorption. Pores with a diameter smaller than 1 nm may be but are generally not present. Further, the catalysts have generally a surface area of at least 10 $m^2/g$, or at least 50 $m^2/g$ or at least 100 $m^2/g$, determined via the B.E.T. method (Brunauer-Emmet-Teller, determined to DIN 66131 by nitrogen adsorption at 77 K). For instance, nickel carbonate has a total pore volume of 0.19-0.39 ml/g or of 0.24-0.35 ml/g determined by nitrogen adsorption and a surface area of 150-400 $m^2/g$ or of 200-370 $m^2/g$ determined by the B.E.T. method. Furthermore, the catalyst particles can have a median particle diameter of at least 50 nm, or at least 100 nm, or not more than 5 mm or not more than 3 mm. In one embodiment, the catalyst particles are generally cylindrical, trilobite, quadrilobate or the like and prepared by cutting an extrudate of the desired profile, e.g., from 1 to 6 mm in diameter and from 2 to 12 mm in length, such as 4 mm long and 2 mm in diameter. In another embodiment, the median particle diameter lies in the range of 0.1-50 microns or in the range of 0.5-50 microns.

In one embodiment, a bulk catalyst composition may be prepared by reacting in a reaction mixture a Group VIII non-noble metal component in solution and a Group VIB metal component in solution or wherein one or both of the metal components are partly in the solid state. The bulk catalyst composition can generally be directly shaped into hydroprocessing particles. If the amount of liquid of the bulk catalyst composition is so high that it cannot be directly subjected to a shaping step, a solid liquid separation can be performed before shaping. Optionally, the bulk catalyst composition, either as such or after solid liquid separation, can be calcined before shaping. The median diameter of the bulk catalyst particles is at least 50 nm, more preferably at least 100 nm, and preferably not more than 5000 μn and more preferably not more than 3000 μm. Even more preferably, the median particle diameter lies in the range of 0.1-50 μm and most preferably in the range of 0.5-50 μm.

If a binder material is used in the preparation of the supported catalyst composition it can be any material that is conventionally applied as a binder in hydroprocessing catalysts. Examples include silica, silica-alumina, such as conventional silica-alumina, silica-coated alumina and alumina-coated silica, alumina such as (pseudo)boehmite, or gibbsite, titania, zirconia, cationic clays or anionic clays such as saponite, bentonite, kaoline, sepiolite or hydrotalcite, or mixtures thereof. Preferred binders are silica, silica-alumina, alumina, titanic, zirconia, or mixtures thereof. These binders may be applied as such or after peptization. It is also possible to apply precursors of these binders that, during the process of the invention are converted into any of the above-described binders. Suitable precursors are, e g., alkali metal aluminates (to obtain an alumina binder), water glass (to obtain a silica binder), a mixture of alkali metal aluminates and water glass (to obtain a silica alumina binder), a mixture of sources of a di-, tri-, and/or tetravalent metal such as a mixture of water-soluble salts of magnesium, aluminum and/or silicon (to prepare a cationic clay and/or anionic clay), chlorohydrol, aluminum sulfate, or mixtures thereof.

In an embodiment, the binder material may be composited with a Group VIB metal and/or a Group VIII non-noble metal, alternatively or additionally to being composited with the bulk catalyst composition and/or prior to being added during the preparation thereof.

Compositing the binder material with any of these metals may be carried out by impregnation of the solid binder with these materials. The person skilled in the art knows suitable impregnation techniques. If the binder is peptized, it is also possible to carry out the peptization in the presence of Group VIB and/or Group VIII non-noble metal components. If alumina is applied as binder, the surface area preferably lies in the range of 100-400 $m^2/g$, or 150-350 $m^2/g$, measured by the B.E.T. method. The pore volume of the alumina in one embodiment is in the range of 0.5-1.5 ml/g measured by nitrogen adsorption.

In one embodiment, the binder material may have less catalytic activity than the bulk catalyst composition or no catalytic activity at all. Consequently, by adding a binder material, the activity of the bulk catalyst composition may be reduced. Therefore, the amount of binder material present may depend on the desired activity of the final catalyst composition. Binder amounts from 0 wt. % to 95 wt. % of the total composition can be present, or in the range of 0.5 wt. % to 75 wt. % of the total catalyst composition.

The catalyst and any binder can be formed into cylindrical pellets in one embodiment. The pellets may have any suitable length and diameter, e.g., in one embodiment a diameter from 2 mm to 12 mm and a length of from 2 mm to 12 mm.

In one embodiment, a basic promoter may be used in the catalyst with the metal compounds, particularly if improved halogen resistance is sought. Promoters include metals form Groups 1-3, including the lanthanide and actinide series, of the periodic table of elements. The promoters in one embodiment are lanthanum, potassium, or a combination thereof. The basic promoters may be used in amounts of 0.25 wt. % to 10 wt. % of the total catalyst, preferably 1 wt. % to 3 wt. %.

In one embodiment the catalyst is presulfided ex situ. Catalyst in the metallic or oxide form can be made as described above, or purchased commercially from a catalyst supplier. The catalyst is sulfided ex situ in a suitable reactor other than the hydrogenation reactor to convert the oxide and/or metallic forms of the catalyst metal compounds to their active sulfide forms. The sulfiding reactor can be located nearby the hydrogenation reactor, or it can be remote. At the sulfiding facility, a sulfiding process is used to convert the catalyst to its active sulfide form. In the case of nickel and tungsten oxides, the sulfiding process converts nickel and tungsten oxides to their active sulfide forms using a sulfiding agent in the presence of hydrogen. according to the following exemplary reactions:

$$3\,NiO + 2\,H_2S + H_2 \longrightarrow Ni_3S_2 + 3\,H_2O \quad (1)$$

$$WO_3 + 2\,H_2S + H_2 \longrightarrow WS_2 + 3\,H_2O. \quad (2)$$

The sulfur compounds that can be used as the sulfiding agent include $H_2S$, carbon disulfide, methyl disulfide, ethyl disulfide, propyl disulfide, isopropyl disulfide, butyl disulfide, tertiary butyl disulfide, thianaphthene, thiophene, secondary dibutyl disulfide, thiols, sulfur containing hydrocarbon oils and sulfides such as methyl sulfide, ethyl sulfide, propyl sulfide, isopropyl sulfide, butyl sulfide, secondary dibutyl sulfide, tertiary butyl sulfide, dithiols and sulfur-bearing gas oils. Any other organic sulfur source that can be converted to $H_2S$ over the catalyst in the presence of hydrogen can be used. The catalyst may also be activated by an organo sulfur process as described in U.S. Pat. No. 4,530,917 and other processes described therein and this description is incorporated by reference into this specification.

Presulfiding services are commercially available to sulfide the catalyst ex situ, for example, using the TOTSUCAT sulfiding process from Eurecat US Inc. (Houston, Tex.) as described in "Eurecat Sulfiding Solutions," Randy Alexander et al. (September 2005), which is hereby incorporated herein by reference in its entirety and available at http://www.eurecat.fr/eurecat/gb/technical_doc/Y509%20Hydrocarbon%20Engineering%20Sept%202005.pdf.

The active catalyst sulfide is sensitive to oxygen (from air), which can re-oxidize the catalyst and render it inactive. Therefore, the sulfided catalyst may be protected from contact with air or passivated. As used herein, passivated catalyst has been protected sufficiently against air oxidation to make reactor loading under air possible. Whether passivated or especially if it is not otherwise passivated, prior to loading, the catalyst is to the extent feasible handled under an inert atmosphere such as nitrogen and kept in sealed, inert gas-purged bins or drums during storage and shipment. As used herein, an inert gas is one which does not react to an appreciable extent with the sulfided catalyst, e.g., nitrogen.

In an embodiment, the porous catalyst is impregnated with an organic compound which is a liquid at the impregnation conditions and which at least partially fills the void space inside in the catalyst particles. This fill liquid provides a diffusion barrier to prevent oxygen from air from penetrating the catalyst and deactivating it. The liquid fill passivation technique may be used alone, in combination with an inert shipping/storage atmosphere, and/or in combination with another passivation technique that may involve treatment of the catalyst before or after liquid impregnation, e.g., as disclosed in U.S. Pat. No. 7,407,909, which is hereby incorporated herein by reference in its entirety.

In one embodiment, the liquid used to protect the catalyst from premature oxidation is a hydrocarbon resin (including oligomers) or a normally liquid olefinic monomer. Normally liquid monomers refer to polymerizable monomers, e.g., olefins and diolefins, having a vapor pressure of less than 1 atmosphere at 25° C. In another embodiment, the hydrocarbon resin may be the same resin or the same type of resin to be hydrogenated with the catalyst in the hydrotreating reactor. The hydrocarbon resin used to passivate the catalyst, where the organic liquid is a hydrocarbon resin, is referred to herein as the fill resin. The fill resin may be a hydrogenated resin with a low unsaturation content, e.g., less than 1 mole percent olefinic hydrogens based on the total hydrogen content of the fill resin. For example, the fill resin may be obtained under the trade designation ESCOREZ, e.g., 1102, 1102F, 1102RM, 1304, 1310LC, 1315, 1401, 2203LC, 2394, 2520, 5300, 5320, 5340, 5380, 5400, 5415, 5490, 5600, 5615, 5620, 5637 and 5690. For purposes of convenience and clarity, the fill material is referred to herein as the fill hydrocarbon resin as an example, but the fill liquid is not necessarily limited thereto.

The term hydrocarbon resin as used in the specification and claims include the known high molecular weight polymers, low molecular weight polymers and oligomers derived from cracked petroleum distillates, coal tar, turpentine fractions and a variety of pure monomers. The number average molecular weight is usually below 10,000 or below 2,000, and physical forms at ambient conditions range from thin or thick viscous liquids to hard, brittle solids. Oligomers refer to dimers, trimers, tetramers, pentamers, hexamers, octamers and the like, including combinations thereof, of olefinic monomers, e.g., olefins and diolefins, and in one embodiment the fill liquid comprises a low molecular weight oligomer-rich stream fractionated from the hydrocarbon resin polymerization reactor effluent. Polymerization feedstreams are derived from hydrocarbon refining and cracking streams via various known means and methods of fractionation. For a description of feedstream derivation, monomer composition, methods of polymerization and hydrogenation, reference may be made to the patents referred to herein and to technical literature, e.g., Hydrocarbon Resins, Kirk-Othmer Encyclopedia of Chemical Technology, v. 13, pp. 717-743 (J. Wiley & Sons, 1995); Encycl. of Poly. Sci. and Eng'g., Vol. 7, pp. 758-782 (J. Wiley & Sons, 1987), and the references cited in both of them. All of these references are incorporated by reference for purposes of US patent practice.

Friedel-Crafts polymerization is generally accomplished by use of known Lewis acid catalysts in a polymerization solvent, and removal of solvent and catalyst by washing and distillation. Since the hydrotreating process is particularly suitable for such Lewis acid catalyzed resins, due to residual halogen containing reaction products from the polymerization process, such resins may also be employed as fill resins to impregnate the catalyst in an embodiment. Preferably the hydrocarbon resin is produced by combining the olefin feed stream in a polymerization reactor with a Friedel-Crafts or Lewis Acid catalyst at a temperature between 0° C. and 200° C. Friedel-Crafts polymerization is generally accomplished by use of known catalysts in a polymerization solvent, and the solvent and catalyst may be removed by washing and distillation. The polymerization process may be batchwise or continuous mode. Continuous polymerization may be accomplished in a single stage or in multiple stages. Thermal catalytic polymerization is also utilized, particularly for aliphatic, cyclo-aliphatic, and aliphatic-aromatic petroleum resins, which may likewise be employed as fill resins in an embodiment.

Suitable hydrocarbon resins may include both aromatic and nonaromatic components. Differences in the hydrocarbon resins are largely due to the olefins in the feedstock from which the hydrocarbon components are derived. The hydrocarbon resin may contain "aliphatic" hydrocarbon components which have a hydrocarbon chain formed from $C_4$-$C_6$ fractions containing variable quantities of piperylene, isoprene, mono-olefins, and non-polymerizable paraffinic compounds. Such hydrocarbon resins are based on pentene, butene, isoprene, piperylene, and contain reduced quantities of cyclopentadiene or dicyclopentadiene. The hydrocarbon resin may also contain "aromatic" hydrocarbon structures having polymeric chains which are formed of aromatic units, such as styrene, xylene, α-methylstyrene, vinyl toluene, and indene.

In one embodiment, the fill hydrocarbon resin includes olefins such as piperylene, isoprene, amylenes, and cyclic components. The hydrocarbon resin may also contain aromatic olefins such as styrenic components and indenic components. Piperylenes are generally a distillate cut or synthetic mixture of $C_5$ diolefins, which include, but are not limited to, cis-1,3-pentadiene, trans-1,3-pentadiene, and mixed 1,3-pentadiene. In general, piperylenes do not include branched $C_5$ diolefins such as isoprene. In one embodiment, the hydrocarbon resin has from 40% to 90% piperylene, or from 50% to 90%, or from 60% to 90% piperylene. In one embodiment, the hydrocarbon resin has from 70% to 90% piperylene.

In one embodiment, the fill hydrocarbon resin is substantially free of isoprene. In another embodiment, the hydrocarbon resin contains up to 15% isoprene, or less than 10% isoprene. In yet another embodiment, the hydrocarbon resin contains less than 5% isoprene. In one embodiment, the hydrocarbon resin is substantially free of amylene. In another embodiment, the hydrocarbon resin contains up to 40% amylene, or less than 30% amylene, or less than 25% amylene. In yet another embodiment, the hydrocarbon resin contains up to 10% amylene.

Cyclics are generally a distillate cut or synthetic mixture of $C_5$ and $C_6$ cyclic olefins, diolefins, and dimers therefrom. Cyclics include, but are not limited to, cyclopentene, cyclopentadiene, dicyclopentadiene, cyclohexene, 1,3-cycylohexadiene, and 1,4-cyclohexadiene. The dicyclopentadiene may be in either the endo or exo form. The cyclics may or may not be substituted. Preferred substituted cyclics include cyclopentadienes and dicyclopentadienes substituted with a $C_1$ to $C_{40}$ linear, branched, or cyclic alkyl group, preferably one or more methyl groups. In one embodiment, the fill hydrocarbon resin may include up to 60% cyclics or up to 50% cyclics. Typical lower limits include at least about 0.1% or at least about 0.5% or from about 1.0% cyclics are included. In at least one embodiment, the hydrocarbon resin may include up to 20% cyclics or more preferably up to 30% cyclics. In a particularly preferred embodiment, the hydrocarbon resin comprises from about 1.0% to about 15% cyclics, or from about 5% to about 15% cyclics.

Aromatics that may be in the hydrocarbon resin include one or more of styrene, indene, derivatives of styrene, and derivatives of indene. Specific representative aromatic olefins include styrene, α-methylstyrene, β-methylstyrene, indene, and methylindenes, and vinyl toluenes. The aromatic olefins are typically present in the fill hydrocarbon resin at from 5 wt. % to 45 wt. %, or from 5 wt. % to 30 wt. %, of the monomers. In another embodiment, the hydrocarbon resin comprises from 10 wt. % to 20 wt. % aromatic olefins. Styrenic components include styrene, derivatives of styrene, and substituted sytrenes. In general, styrenic components do not include fused-rings, such as indenics. In one embodiment, the fill hydrocarbon resin comprises up to 60% styrenic components or up to 50% styrenic components. In one embodiment, the hydrocarbon resin comprises from 5% to 30% styrenic components, or from 5% to 20% styrenic components. In an embodiment, the hydrocarbon resin comprises from 10% to 15% styrenic components. The hydrocarbon resin may comprise less than 15% indenic components, or less than 10% indenic components. Indenic components include indene and derivatives of indene. In one embodiment, the hydrocarbon resin comprises less than 5% indenic components. In another embodiment, the hydrocarbon resin is substantially free of indenic components.

The fill hydrocarbon resin may have a viscosity that facilitates introducing the hydrocarbon resin onto and impregnating the sulfide catalyst. In an embodiment, fill hydrocarbon resins have melt viscosity of from 300 to 800 centipoise (cPs) at 160° C., or from 350 to 650 cPs at 160° C. In an embodiment, the hydrocarbon resin melt viscosity is from 375 to 615 cPs at 160° C., or from 475 to 600 cPs at 160° C. The melt viscosity may be measured by a Brookfield viscometer with a type "J" spindle, ASTM D6267.

Generally the fill hydrocarbon resins have a weight average molecular weight (Mw) greater than about 300 g/mole, or greater than 600 g/mole or greater than about 1000 g/mole.

In at least one embodiment, hydrocarbon resins have a weight average molecular weight (Mw) of from 300 to 10,000 g/mole, or from 300 to 3000 g/mole, or from 300 to 2000 g/mole. The hydrocarbon resin in one embodiment may have a number average molecular weight (Mn) of from 450 to 700 g/mole. The hydrocarbon resin may have a z-average molecular weight (Mz) of from 5000 to 10,000 g/mole, or from 6000 to 8000 g/mole. Mw, Mn, and Mz may be determined by gel permeation chromatography (GPC).

In one embodiment, the fill hydrocarbon resin has a polydispersion index ("PDI", PDI=Mw/Mn) of 4 or less. In an embodiment, the hydrocarbon resin has a PDI of from 2.6 to 3.1.

The fill hydrocarbon resins may have a glass transition temperature (Tg) of from about −30° C. to about 100° C., or from about 0° C. to about 80° C., or from about 40° C. to about 60° C., or from about 45° C. to about 55° C., or from about 48° C. to about 53° C. Differential scanning calorimetry (DSC) may be used to determine the Tg of the hydrocarbon resin.

Natural resins can also be used as the fill resin and/or hydrotreated in accordance herewith. The natural resins are traditional materials documented in the literature, see for example, Encycl. of Poly. Sci. and Eng'g., Vol. 14, pp. 438-452 (John Wiley & Sons, 1988).

The rosins capable of impregnating the catalyst and/or hydrotreating with the filled catalyst in accordance herewith include any of those known in the art to be suitable as tackifying agents, specifically including the esterified rosins. The principal sources of the rosins include gum rosins, wood rosin, and tall oil rosins which typically have been extracted or collected from their known sources and fractionated to varying degrees. Additional background can be obtained from technical literature, e.g., Kirk-Othmer Encycl. of Chem. Tech., Vol. 17, pp. 475-478 (John Wiley & son, 1968) and Handbook of Pressure-Sensitive Adhesive Technology, ed. by D. Satas, pp. 353-356 (Van Nostrand Reinhold Co., 1982).

The catalyst particles may be filled by contacting the catalyst particles with the fill resin or other liquid under conditions wherein the fill material is liquid. Fill resins or other fill material which have a low softening point or melting point and a low melt viscosity may be used at ambient or elevated temperatures, e.g., up to 140° C., or up to 120° C., or up to 100° C., or up to 80° C., or up to 60° C., or up to 40° C. The temperature should be sufficiently low so as to avoid excessive catalytic activity or denaturing of the catalyst.

The contact may be in a tumbler, conveyor or other suitable apparatus in one embodiment by spraying the liquid onto the catalyst particles at a sufficient rate until the liquid is sufficiently absorbed into the pores of the catalyst particles. The tumbler apparatus should be sufficiently gentle so as to avoid the formation of catalyst fines. In one embodiment, the pore volume of the catalyst is only partially filled so as to maintain a dry character of the catalyst, which allows free catalyst flow and avoids agglomeration. In an embodiment the fill resin fills from 50% to 100% of the pore volume of the catalyst particles, or from 60% to 99%, or from 70% to 98%, or from 80% to 95%, or from 90% to 95% of the pore volume of the catalyst particles. The filling process may be operated batchwise, semi-batch, or continuously.

The partially filled catalyst particles may be optionally screened to remove fines. However, in one embodiment, the partially filled catalyst particles have improved crush strength which reduces attrition and fines formation, and screening to remove fines may not be needed.

The partially filled catalyst particles in an embodiment are stored and/or shipped in a suitable container or package which can maintain an inert atmosphere, e.g., nitrogen-purged and/or padded bins or drums, provided with suitably sealable openings to introduce and/or remove the catalyst particles. The catalyst particles may be conveniently stored and shipped in the same container, or may be transferred between storage and shipping containers before or after transport. In one embodiment, the same shipping and/or storage container may also be used to apply the hydrocarbon resin to the catalyst particles.

The presulfided and/or partially filled catalyst particles are loaded, e.g., from the storage and/or shipping containers, into hydrogenation reactors using conventional catalyst loading equipment and techniques. Due to the increased strength of the partially filled catalyst particles, much less dust is formed and exposure of personnel to dust is reduced and in one embodiment, procedures intended to ameliorate dust creation and/or exposure may be relaxed during the catalyst loading. Moreover, pressure drop through the loaded catalyst bed is reduced due to the presence of less fines relative to the loading of unfilled catalyst particles, et ceteris paribus.

In an embodiment, the presulfided and/or partially filled catalyst can be used to hydrogenate any organic compound capable of catalytic hydrogenation or reduction, such as, for example, alkenes, alkynes, aldehydes, ketones, esters, imines, amides, nitriles, nitro compounds, sulfo compounds, combinations thereof, and the like, and also including mixtures of such organic compounds in or with other compounds that are generally inert to hydrogenation. In one specific embodiment, the presulfided and/or partially filled catalyst is used to hydrogenate a hydrocarbon resin. The hydrocarbon resins which are hydrogenated may be any of the hydrocarbon resins discussed above that are used to impregnate the presulfided catalyst. In one embodiment, the fill hydrocarbon resin and the hydrocarbon resin that is hydrogenated are the same, and in another embodiment they are different. The hydrogenation of the hydrocarbon resin may be carried out by any method known in the art, and the invention is not limited by the method of hydrogenation. For example, the hydrogenation of the hydrocarbon resin may be either a batchwise or a continuous process.

Generic hydrogenation treating conditions include reactions in the temperature of about 100° C. to about 350° C. and pressures of between five atmospheres (506 kPa) and 300 atm (30.4 MPa) hydrogen, for example, 10 atm to 275 atm (1.01 MPa to 27.6 MPa). In one embodiment, the temperature is in the range including 180° C. and 320° C. and the pressure is in the range including 15.2 MPa and 20.3 MPa hydrogen. The hydrogen to feed volume ratio to the reactor under standard conditions (25° C., 1 atm pressure) typically can range from 20 to 200, for water-white resins 100 to 200 is preferred.

Catalyst activity decreases over time due to carbonaceous deposition onto the catalyst support, and this can be periodically eliminated or removed by regenerating the catalyst bed with high pressure hydrogen at temperatures between about 310° C. to about 350° C. High pressure here means, for example, at least about 180 bar. This regeneration is best accomplished in the absence of hydrocarbon feed to the reactor, e.g., during interruption of the hydrogenation process.

Hydrogenated polymeric resins of the invention specifically include hydrocarbon resins suitable as tackifiers for adhesive compositions, particularly adhesive compositions comprising polymeric base polymer systems of either natural or synthetic elastomers, including such synthetic elastomers as those from styrene block copolymers, olefinic rubbers, olefin derived elastomers or plastomers, and various copolymers having elastomeric characteristics, e.g., ethylene-vinyl ester copolymers. Such adhesive compositions find particular utility in hot melt adhesive and pressure sensitive adhesive applications such as those for adhesive tapes, diaper tabs, envelopes, note pads, and the like. Often compatibility of the tackifier with polymeric base polymer systems is best achieved by selection of a hydrocarbon resin that is high in aromatic monomer content. Concurrently it is sought to select a tackifier that has color characteristics commensurate with those of the base polymer system, preferably both the polymer system and its tackifier will be essentially transparent and low in chromophores, that is, color. Retention of this low color characteristic is important during heating operations such as those present in formulation by melt processing and application of the adhesive compositions to substrate materials under elevated temperatures. Adequate hydrogenation is known to achieve desirable heat stability of low color properties in polymeric hydrocarbon resins made from either aliphatic or aromatic monomers, or mixes thereof. Both objectives can be achieved by use of the process of the present invention.

Accordingly, the invention provides the following embodiments:

A. A packaged, presulfided catalyst useful to hydrogenate hydrocarbon resin without an in situ sulfiding step, comprising:
- porous catalyst particles comprising a metal catalyst structure comprising an internal pore volume with presulfided interstitial surfaces;
- an organic liquid at least partially filling the pore volume; and
- a container housing the catalyst particles in an inert atmosphere.

B. A method to hydrogenate hydrocarbon resin, comprising:
- preparing catalyst particles comprising a metal catalyst structure comprising an internal pore volume with oxidized interstitial surfaces;
- sulfiding the supported metal catalyst structure to form presulfided interstitial surfaces;
- contacting the presulfided catalyst particles with an organic liquid to at least partially fill the pore volume and improve a crush strength of the catalyst particles; optionally screening the resin-filled catalyst particles to remove fines;
- sealing the resin-filled catalyst particles in a container housing the catalyst particles in an inert atmosphere;
- loading the resin-filled catalyst particles from the container into a hydrogenation reactor; and
- immediately (without a separate in situ sulfiding step) contacting the catalyst in the reactor with a catalytically hydrogenatable or reducible organic compound under hydrogenation conditions to hydrogenate the organic compound.

C. A packaged, presulfided catalyst useful to hydrogenate hydrocarbon resin without an in situ sulfiding step, comprising:
- porous catalyst particles comprising a supported metal catalyst structure comprising an internal pore volume with presulfided interstitial surfaces;
- about 20 wt. % of a low molecular weight hydrocarbon resin, based on the weight of the supported metal catalyst structure, filling from 90 to 95 percent of the pore volume to improve a crush strength of the catalyst particles; and
- an air-tight, transportable container housing the discrete catalyst particles in an inert atmosphere.

D. A method to hydrogenate hydrocarbon resin, comprising:
- preparing catalyst particles comprising a supported metal catalyst structure comprising an internal pore volume with oxidized interstitial surfaces;
- sulfiding the supported metal catalyst structure to form presulfided interstitial surfaces;
- in an inert atmosphere, contacting the presulfided catalyst particles with about 20 wt. % of a low molecular weight hydrocarbon resin, based on the weight of the presulfided catalyst particles, to fill from 90 to 95 percent of the pore volume and improve a crush strength of the catalyst particles;
- optionally screening the resin-filled catalyst particles to remove fines;
- sealing the resin-filled catalyst particles in an air-tight, transportable container housing the discrete catalyst particles in an inert atmosphere;
- loading the resin-filled catalyst particles from the container into a catalyst bed in a hydrogenation reactor; and
- immediately (without a separate in situ sulfiding step) contacting the catalyst bed with an unsaturated hydrocarbon resin under hydrogenation conditions to hydrogenate the unsaturated hydrocarbon resin.

EXAMPLE

Various lengths of presulfided 5 mm diameter catalyst particles (UCI T-2601 E), both unfilled and partially filled at 90% to 95% pore volume with an ESCOREZ 5000 series hydrocarbon resin were tested for crush strength in accordance with ASTM D4179. The results shown in FIG. 1 indicate that the liquid-filled catalyst particles have a higher crush strength and will suffer less attrition during handling, storage, shipment, loading, etc. The filled catalyst particles were loaded into a reactor and successfully used to hydrogenate ESCOREZ 5000 series resins in a commercial facility without in situ sulfiding. The catalyst is charged to the reactor 3 or 4 times a year, and saving about 2 days of sulfiding time at each loading, thus improving annual production run time by 6 to 8 days. In addition, there is no need to have sulfur compounds on site for sulfidation, no hydrogen sulfide off gas formed during sulfidation, less dust is generated during catalyst loading, corrosion byproducts introduced into the reactor and equipment during sulfiding are reduced, and less pressure drop is seen in the catalyst bed due to a reduction of foulant materials formed during handling relative to an unfilled catalyst or during in situ sulfiding.

All documents described herein are incorporated by reference herein, including any patent applications and/or testing procedures to the extent that they are not inconsistent with this application and claims. The principles, preferred embodiments, and modes of operation of the present invention have been described in the foregoing specification. Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

We claim:

1. A packaged, presulfided catalyst useful to hydrogenate hydrocarbon resin without an in situ sulfiding step, comprising:
- porous catalyst particles comprising a supported metal catalyst structure comprising an internal pore volume with presulfided interstitial surfaces;
- about 20 wt. % of a low molecular weight hydrocarbon resin, based on the weight of the supported metal catalyst structure, filling from 90 to 95 percent of the pore volume to improve a crush strength of the catalyst particles; and
- an air-tight, transportable container housing the discrete catalyst particles in an inert atmosphere.

2. A method to hydrogenate hydrocarbon resin, comprising:
- preparing catalyst particles comprising a supported metal catalyst structure comprising an internal pore volume with oxidized interstitial surfaces;
- sulfiding the supported metal catalyst structure to form presulfided interstitial surfaces;
- in an inert atmosphere, contacting the presulfided catalyst particles with about 20 wt. % percent of a low molecular weight hydrocarbon resin, based on the weight of the presulfided catalyst particles, to fill from 90 to 95 percent of the pore volume and improve a crush strength of the catalyst particles;

optionally screening the resin-filled catalyst particles to remove fines;

sealing the resin-filled catalyst particles in an air-tight, transportable container housing the discrete catalyst particles in an inert atmosphere;

loading the resin-filled catalyst particles from the container into a catalyst bed in a hydrogenation reactor; and immediately (without a separate in situ sulfiding step) contacting the catalyst bed with an unsaturated hydrocarbon resin under hydrogenation conditions to hydrogenate the unsaturated hydrocarbon resin.

* * * * *